United States Patent [19]

Kunisch et al.

[11] Patent Number: 5,276,169
[45] Date of Patent: Jan. 4, 1994

[54] ANTIMYCOTIC CARBONYL- AND AMINO-SUBSTITUTED TETRAHYDROFURANS

[75] Inventors: Franz Kunisch, Odenthal-Glöbusch; Joachim Mittendorf, Wuppertal; Manfred Plempel, Haan, all of Fed. Rep. of Germany

[73] Assignee: Bayer Aktiengesellschaft, Leverkusen, Fed. Rep. of Germany

[21] Appl. No.: 959,838

[22] Filed: Oct. 13, 1992

[30] Foreign Application Priority Data

Oct. 22, 1991 [DE] Fed. Rep. of Germany ....... 4134758

[51] Int. Cl.$^5$ ................... C07D 307/14; A61K 31/34
[52] U.S. Cl. .................................................... 549/480
[58] Field of Search ...................... 549/480; 514/472

[56] References Cited

U.S. PATENT DOCUMENTS 2,432,016 12/1947 Hofmann ............................. 260/345
4,054,585 10/1977 Felauer et al. ..................... 260/347.3
4,309,436 1/1982 Eckhardt ............................. 424/272

OTHER PUBLICATIONS

Shiozaki et al.; Agric. Biol. Chem., 52(8), pp. 2027-2034, 1988.
Bonora et al., Int. J. Pept. Prot. Res. 17, 181 (1981).
Beilstein E IV 11, p. 26 (1983).
Polym. J. 7, 72 (1975).
JACS, 77, 1055, (1955).
J. Chem. Soc., Perkin Trans II(6), 875 (1988).
J. Macromol. Sci, Chem. A 13, (4), 477 (1979).
JACS. 77, 4069 (1955).
Tetrahedron, vol. 26, No. 15, 1970, Oxford GB, pp. 3849–3856, H. Wamhoff, "Heterocyclische beta–Enaminoester-III. NMR- ... ".
Tetrahedron, vol. 47, No. 27, Jul. 1, 1991, Oxford GB, pp. 4861–4868, M.-CH. Cheng et al. "3-Amino-2,-3-deoxy-d-erythro-furanose Derivatives", p. 4862, Schema 1.
Patent Abstracts of Japan, vol. 012, No. 410 (C–540) 1988 & JP-A-63 150 271 (Sankyo Co. Ltd.).
Derwent Abstr. JP 297945 (J6 3150-271-A) 1988.
J. C. Sheehan et al., J. Am. Chem. Soc. 95, 875 (1973).
F. E. Frerman et al., J. Biol. Chem. 255, No. 5, pp. 2199-2202 (1980).
Benoiton et al., Int. J. Pept. Prot. Res. 13, 403 (1979).

Primary Examiner—Marianne M. Cintins
Assistant Examiner—Michael B. Hydorn
Attorney, Agent, or Firm—Sprung Horn Kramer & Woods

[57] ABSTRACT

Novel antimycotic carbonyl- and amino-substituted tetrahydrofurans of the formula

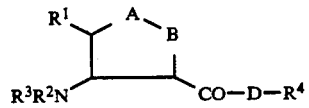

in which
one of A and B is an oxygen atom and the other -CHR$^5$,
D is O, S or NH, and
R$^1$, R$^2$, R$^3$ R$^4$ and R$^5$ each independently is hydrogen or an organic radical.

5 Claims, No Drawings

ANTIMYCOTIC CARBONYL- AND AMINO-SUBSTITUTED TETRAHYDROFURANS

The invention relates to new substituted tetrahydrofurans, processes for their preparation and their use as medicaments, in particular as antimycotic medicaments.

It is already known that 2-amino-3-homofuranosides have an antibacterial action [cf. JP 29 79 45 (J6-3150-271-A)]

The compounds 2-amino-3-ethoxycarbonyl-dihydrofuran and 2-amino-3-ethoxycarbonyl-4-methyl-4,5-dihydrofuran in the form of the conjugated acids of the corresponding enamino esters are furthermore described in the publication Tetrahedron 26 (15), 3849-56.

The invention now relates to new substituted tetrahydrofurans of the general formula (I)

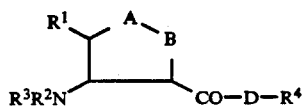

in which

A and B are always different and represent an oxygen atom, or represent the group of the formula -CHR$^5$,
wherein R$^5$ denotes hydrogen or straight-chain or branched alkyl having up to 8 carbon atoms, which is optionally substituted by halogen, hydroxyl, phenyl or carboxyl or by straight-chain or branched alkoxy or alkoxycarbonyl having in each case up to 6 carbon atoms, R$^1$ represents hydrogen, or represents straight-chain or branched alkyl having up to 8 carbon atoms, which is optionally mono- or disubstituted by identical or different substituents, which may be halogen, hydroxyl, phenyl or carboxyl, or by straight-chain or branched alkoxy, acyl or alkoxycarbonyl having in each case up to 6 carbon atoms, or by a group of the formula -NR$^6$R$^7$,
wherein R$^6$ and R$^7$ are identical or different and denote hydrogen, phenyl or straight-chain or branched alkyl having up to 6 carbon atoms, R$^2$ represents hydrogen, or represents straight-chain or branched alkyl having up to 8 carbon atoms, which is optionally mono- or disubstituted by identical or different substituents, which may be hydroxyl or formyl, or by straight-chain or branched acyl having up to 6 carbon atoms, or by phenyl or benzoyl, which are optionally mono- or disubstituted by identical or different substituents, which may be halogen, nitro or cyano, or by straight-chain or branched alkyl having up to 6 carbon atoms,
or
represents straight-chain or branched acyl having up to 8 carbon atoms,
or
represents benzoyl, which is optionally substituted as described above,
or
represents a group of the formula -SO$_2$R$^8$,
wherein R$^8$ denotes straight-chain or branched alkyl having up to 8 carbon atoms, benzyl or phenyl, the latter optionally being mono-, di- or tri-substituted by identical or different substituents, which may be halogen, hydroxyl, nitro, cyano, trifluoromethyl or trifluoromethoxy, or by straight-chain or branched alkyl, alkoxy or alkoxycarbonyl having in each case up to 6 carbon atoms or carboxyl, or by the abovementioned group -NR$^6$R$^7$,
wherein R$^6$ and R$^7$ have the abovementioned meaning,
or represents phenyl, which is optionally mono-, di- or trisubstituted by identical or different substituents, which may be halogen, hydroxyl, nitro, trifluoromethyl, trifluoromethoxy or straight-chain or branched alkyl, acyl, alkoxy or alkoxycarbonyl having in each case up to 6 carbon atoms, or by a group of the formula -NR$^6$R$^7$ or -S$_2$R$^3$,
wherein R$^6$, R$^7$ and R$^8$ have the abovementioned meaning, R$^3$ represents hydrogen, or represents straight-chain or branched alkyl having up to 8 carbon atoms, which is optionally substituted by phenyl,
or R$^2$ and R$^3$ together represent the radical of the formula =CHR$^{5'}$,
wherein R$^{5'}$ has the abovementioned meaning of R$^5$ and is identical to or different from this, D represents an oxygen or sulphur atom, or represents the

group, and

R$^4$ represents hydrogen, or represents straight-chain or branched alkyl having up to 8 carbon atoms or phenyl, the latter optionally being mono-, di- or trisubstituted by identical or different substituents, which may be hydroxyl, halogen, nitro, cyano, carboxyl, trifluoromethyl or trifluoromethoxy, by straight-chain or branched alkoxy, and in the case of phenyl also by alkyl, acyl or alkoxycarbonyl having in each case up to 6 carbon atoms, or by a group of the formula -NR$^6$R$^7$ or -SO$_2$R$^8$,
wherein R$^6$, R$^7$ and R$^8$ have the abovementioned meaning,
or, in the case where D represents the

group,

R$^4$ represents the group of the formula -SO$_2$R$^8$
wherein

R$^8$ has the abovementioned meaning,
if appropriate in an isomeric form, and acid addition salts and metal salt complexes thereof.

The compounds according to the invention can also be in the form of their salts. Salts with organic or inorganic bases or acids may be mentioned in general here. The acids which can be added on include, preferably, hydrohalic acids, such as, for example, hydrochloric acid and hydrobromic acid, in particular hydrochloric acid, and furthermore phosphoric acid, nitric acid, sulphuric acid, mono- and bifunctional carboxylic acids and hydroxycarboxylic acids, such as, for example, acetic acid, maleic acid, malonic acid, oxalic acid, gluconic acid, succinic acid, fumaric acid, tartaric acid, citric acid, salicylic acid, sorbic acid and lactic acid, as well as sulphonic acids, such as, for example, p-toluenesulphonic acid, 1,5-naphthalenedisulphonic acid or camphorsulphonic acid.

Physiologically acceptable salts can likewise be metal or ammonium salts of the compounds according to the invention which have a free carboxyl group. Particularly preferred salts are, for example, salts of sodium, potassium, magnesium or calcium, as well as ammonium salts, which are derived from ammonia or organic amines, such as, for example, ethylamine, di- or triethylamine, di- or triethanolamine, dicyclohexylamine, dimethylaminoethanol, arginine, lysine or ethylenediamine.

The compounds according to the invention can exist in stereoisomeric forms, for example either as mirror images (enantiomers) or those forms which do not have behave as mirror images (diastereomers), or can be present as a diastereomer mixture or as pure cis or trans isomers. The invention relates both to the antipodes, racemic forms and diastereomer mixtures and to the pure isomers. Like the diabtereomers, the racemic forms can be separated into the stereoisomerically uniform constituents in a known manner (compare E. L. Eliel, Stereochemistry of Carbon Compounds, McGraw Hill, 1962]. Separation into the stereoisomerically uniform compounds is carried out, for example, via chromatographic racemate cleavage of diastereomeric esters and amides or on optically active phases. Crystallisation of diastereomeric salts is furthermore possible.

Preferred compounds of the general formula (I) are those in which

A and B are always different and represent an oxygen atom, or represent the group of the formula $-CHR^5$
wherein $R^5$ denotes hydrogen or straight-chain or branched alkyl having up to 6 carbon atoms, which is optionally substituted by halogen or hydroxyl or by straight-chain or branched alkoxy or alkoxycarbonyl having in each case up to 4 carbon atoms, $R^1$ represents hydrogen, or represents straight-chain or branched alkyl having up to 6 carbon atoms, which is optionally substituted by halogen or hydroxyl, by straight-chain or branched alkoxy, acyl or alkoxycarbonyl having in each case up to 4 carbon atoms, or by a group of the formula $-NR^6R^7$,
wherein $R^6$ and $R^7$ are identical or different and denote hydrogen or straight-chain or branched alkyl having up to 4 carbon atoms, $R^2$ represents hydrogen, or represents straight-chain or branched alkyl having up to 6 carbon atoms, which is optionally substituted by hydroxyl or formyl, or by straight-chain or branched acyl having up to 4 carbon atoms, or by phenyl or benzoyl, which are optionally substituted by halogen, nitro or cyano, or by straight-chain or branched alkyl having up to 4 carbon atoms, or represents straight-chain or branched acyl having up to 6 carbon atoms, or represents benzoyl, which is optionally substituted as described above, or represents a group of the formula $-SO_2R^8$,
wherein $R^8$ denotes straight-chain or branched alkyl having up to 6 carbon atoms, phenyl or benzyl, the latter optionally being mono- or disubstituted by identical or different substituents, which may be halogen, hydroxyl, nitro, cyano, trifluoromethyl or trifluoromethoxy, or by straight-chain or branched alkyl or alkoxy having in each case up to 4 carbon atoms, or by the abovementioned group of the formula $-NR^6R^7$,
wherein $R^6$ and $R^7$ have the abovementioned meaning, or represents phenyl, which is optionally mono- or disubstituted by identical or different substituents, which may be halogen, hydroxyl, nitro, trifluoromethyl, trifluoromethoxy or straight-chain or branched alkyl, acyl, alkoxy or alkoxycarbonyl having in each case up to 4 carbon atoms, or by a group of the formula $-NR^6R^7$ or $-SO_2R^8$,
wherein $R^6$, $R^7$ and $R^8$ have the abovementioned meaning, $R^3$ represents hydrogen, or represents straight-chain or branched alkyl having up to 6 carbon atoms or benzyl, or $R^2$ and $R^3$ together represent the radical of the formula $=CHR^{5'}$,
wherein $R^{5'}$ has the abovementioned meaning of $R^5$ and is identical to or different from this, D represents an oxygen or sulphur atom, or represents the

group, and $R^4$ represents hydrogen, or represents straight-chain or branched alkyl having up to 6 carbon atoms or phenyl, the latter optionally being mono- or disubstituted by identical or different substituents, which may be hydroxyl, halogen, nitro, cyano, trifluoromethyl or trifluoromethoxy, or by straight-chain or branched alkoxy, acyl or alkoxycarbonyl having in each case up to 4 carbon atoms, or by a group of the formula $-NR^6R^7$ or $-SO_2R^8$,
wherein $R^6$, $R^7$ and $R^8$ have the abovementioned meaning, or in the case where D represents the

group, $R^4$ represents the group of the formula $-SO_2R^8$,
wherein $R^8$ has the abovementioned meaning, if appropriate in an isomeric form, and acid addition salts and metal salt complexes thereof.

Particularly preferred compounds of the general formula (I) are those
in which

A and B are always different and represent an oxygen atom, or represent the group of the formula $-CHR^5$,
wherein $R^5$ denotes hydrogen or straight-chain or branched alkyl having up to 4 carbon atoms, $R^1$ represents hydrogen, or represents straight-chain or branched alkyl having up to 4 carbon atoms, $R^2$ represents hydrogen, or represents straight-chain or branched alkyl having up to 4 carbon atoms, or represents straight-chain or branched acyl having up to 4 carbon atoms, or represents a group of the formula -SO$_2$R$^8$, wherein $R^8$ denotes straight-chain or branched alkyl having up to 4 carbon atoms, phenyl or benzyl, the latter optionally being substituted by hydroxyl, fluorine, chlorine, bromine, nitro, cyano, methyl, ethyl or methoxy, $R^3$ represents hydrogen, or represents straight-chain or branched alkyl having up to 4 carbon atoms, or $R^2$ and $R^3$ together represent the radical of the formula =CHR$^{5'}$, wherein $R^{5'}$ has the abovementioned meaning of $R^5$ and is identical to or different from this, D represents an oxygen or a sulphur atom, or represents the

group, $R^4$ represents hydrogen, or represents straight-chain or branched alkyl having up to 4 carbon atoms or phenyl, the latter optionally being substituted by fluorine, chlorine, bromine, nitro, cyano, methoxy or ethoxy, or by a group of the formula -NR$^6$R$^7$ or -SO$_2$R$^8$, wherein $R^6$ and $R^7$ are identical or different and denote hydrogen, methyl or ethyl and $R^8$ has the abovementioned meaning, or, in the case where D represents the

group, $R^4$ represents the group of the formula -SO$_2$R$^8$, wherein $R^8$ has the abovementioned meaning, if appropriate in an isomeric form, and acid addition salts and metal salt complexes thereof.

Especially preferred compounds of the general formula (I) are those in which the two substituents -NR$_2$R$^3$ and —CO—D—R$^4$ are in the cis-position.

A process has furthermore been found for the preparation of the compounds of the general formula (I) according to the invention, characterised in that

[A] in the case where A represents the -CHR$^5$ group and B represents an oxygen atom, compounds of the general formula (II)

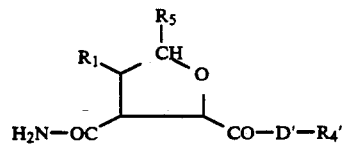

in which $R^1$ and $R^5$ have the abovementioned meaning,

D' represents an oxygen atom and $R^{4'}$ represents C$_1$-C$_5$-alkyl, are first converted in an oxidative rearrangement with oxidising agents, preferably lead tetraacetate and alcohols (R$^9$-OH) in the presence of a catalyst, preferably triethylamine, into the compounds of the general formula (III)

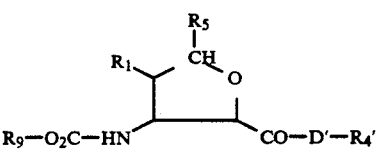

in which $R^1$, $R^{4'}$, $R^5$ and D' have the abovementioned meaning and $R^9$ represents a (C$_1$-C$_5$)-alkyl radical of the corresponding alcohol (R$^9$-OH), and preferably represents tert.butyl, and the corresponding acid addition salts, preferably the hydrochlorides, are then liberated in inert solvents in the presence of an acid, preferably hydrochloric acid, the ester radical (-CO$_2$R$^9$) being split off, or

[B] in the case where A represents an oxygen atom and B represents the -CHR$^5$ group, compounds of the general formula (IV)

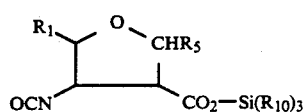

in which $R^1$ and $R^5$ have the abovementioned meaning and $R^{10}$ represents a C$_1$-C$_3$-alkyl radical, are first reacted in ethers, preferably diethyl ether, in the presence of water to give the compounds of the general formula (V)

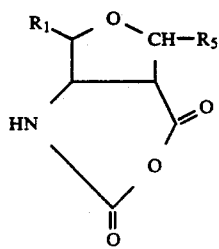

in which $R^1$ and $R^5$ have the abovementioned meaning, and in the next step these compounds are converted with acids, preferably hydrochloric acid, and subsequently propylene oxide, the ring being opened, into the compounds of the general formula (Ia)

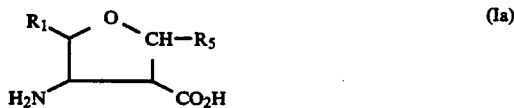

in which

R[1] and R[5] have the abovementioned meaning, in the case of the esters, the acids are esterified by the customary method, in the case of the acids [(I)→D=O; R[4]=H), if appropriate the corresponding esters are also hydrolysed by the customary method, and in the case of the other radicals mentioned above for D and R[4], derivatives are formed, likewise by customary processes, such as, for example, amidation, sulphonation or sulphonamidation, if appropriate in the presence of auxiliaries, such as catalysts and dehydrating agents, starting from the corresponding carboxylic acids, if appropriate with prior activation.

The processes according to the invention can be illustrated by way of example by the following equation:

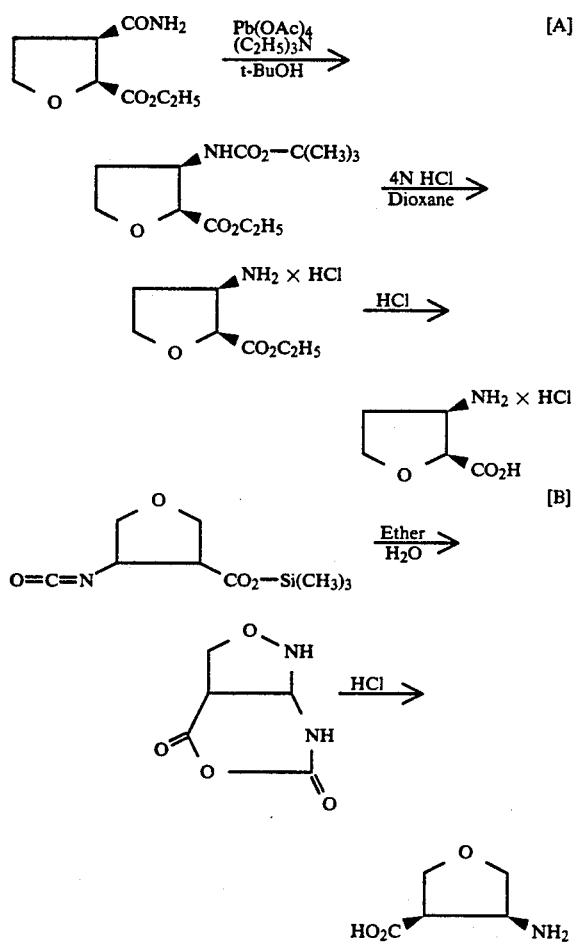

Suitable solvents for processes [A] and [B] are water and all the inert organic solvents which do not change under the reaction conditions. These include, preferably, alcohols, such as reethanol, ethanol, propanol and isopropanol, ethers, such as diethyl ether, dioxane, tetrahydrofuran, glycol monomethyl ether or glycol dimethyl ether, or amides, such as dimethylformamide, dimethylacetamide or hexamethylphosphoric acid triamide, or glacial acetic acid, dimethylsulphoxide, acetonitrile or pyridine. Ethanol, tetrahydrofuran, dioxane and diethyl ether are preferred.

The reaction temperatures can be varied within a substantial range. The reaction is in general carried out at between +100° C. and +150° C., preferably between +20° C. and 100° C., in particular at the boiling point of the particular solvent. The reactions can be carried out under normal pressure, and also under increased or reduced pressure (for example 0.5 to 3 bar). They are in general carried out under normal pressure.

In carrying out process variants [A] and [B] according to the invention, any desired ratio of substances participating in the reaction can be used. In general, however, molar amounts of the reactants are used. The substances according to the invention are preferably isolated and purified by a procedure in which the solvent is distilled off in vacuo and the crystalline residue obtained, if appropriate only after cooling with ice, is recrystallised from a suitable solvent. In some cases, it may be necessary to purify the compounds according to the invention by chromatography.

Suitable oxidising agents are, for example, hypohalides, such as [bis-(trifluoroacetoxy)-iodo)benzene, (hydroxy-p-toluenesulphonyloxyiodanyl)-benzene, iodobenzene diacetate, iodosylbenzene or lead tetraacetate. Lead tetraacetate is preferred.

Suitable catalysts for the oxidative rearrangement are bases, such as organic amines, tin(IV) chloride or di-n-butyltin dilaurate, preferably organic amines. The reaction also proceeds without a catalyst.

Suitable bases are organic amines (trialkyl($C_1$-$C_6$)amines, such as, for example, triethylamine, or heterocyclic compounds, such as pyridine, methylpiperidine, piperidine or morpholine. Triethylamine is preferred.

Mineral acids are in general employed as the acids. Acids which are preferably employed here are hydrochloric acid, hydrobromic acid, sulphuric acid, phosphoric acid or mixtures of the acids mentioned. Hydrochloric acid is preferred.

The catalysts are in general employed in an amount of 0 mol to 10 mol, preferably 1.5 mol to 3.5 mol, per mole of the compounds of the general formula (II).

The acid is in general employed in an amount of 2 mol to 30 mol, preferably 5 mol to 15 mol, in each case per mole of the compounds of the general formulae (III) and (V).

The hydrolysis of the carboxylic acid esters is carried out by customary methods, by treating the esters with customary bases in inert solvents, it being possible for the salts initially formed to be converted into the free carboxylic acids by treatment with acid.

The hydrolysis of the carboxylic acid esters can likewise be carried out with one of the abovementioned acids.

Suitable bases for the hydrolysis are the customary inorganic bases. These include, preferably, alkali metal hydroxides or alkaline earth metal hydroxides, such as, for example, sodium hydroxide, potassium hydroxide or barium hydroxide, or alkali metal carbonates, such as sodium or potassium carbonate or sodium bicarbonate, or alkali metal alcoholates, such as sodium ethanolate, sodium methanolate, potassium ethanolate, potassium methanolate or potassium tert.-butanolate. Sodium hydroxide or potassium hydroxide are particularly preferably employed.

Suitable solvents for the hydrolysis are water or the organic solvents which are customary for hydrolysis. These include, preferably, alcohols, such as reethanol, ethanol, propanol, isopropanol or butanol, or ethers, such as tetrahydrofuran or dioxane, or dimethylformamide or dimethylsulphoxide. Alcohols, such as reethanol, ethanol, propanol or isopropanol, are particularly preferably used. It is also possible to employ mixtures of the solvents mentioned.

The hydrolysis is in general carried out in a temperature range from 0° C. to +100° C., preferably from +20° C. to +80° C.

The hydrolysis is in general carried out under normal pressure. However, it is also possible to carry out the hydrolysis under reduced pressure or under increased pressure (for example from 0.5 to 5 bar).

In carrying out the hydrolysis, the base or the acid is in general employed in an amount of 1 to 3 mol, preferably 1 to 1.5 mol, per mole of the ester. Molar amounts of the reactants are particularly preferably used.

In carrying out the reaction, the salts of the compounds according to the invention are formed in the first step as intermediate products, which can be isolated. The acids according to the invention are obtained by treatment of the salts with customary inorganic acids. These include, preferably, mineral acids, such as, for example, hydrochloric acid, hydrobromic acid, sulphuric acid or phosphoric acid. It has proved advantageous in the preparation of the carboxylic acids to acidify the basic reaction mixture of the hydrolysis in a second step, without isolation of the salts. The acids can then be isolated in the customary manner.

Amidation and sulphonation or sulphonamidation will be explained here as examples of the abovementioned derivatisation possibilities.

The amidation is in general carried out in inert solvents in the presence of a base and of a dehydrating agent.

Suitable solvents here are inert organic solvents which do not change under the reaction conditions. These include halogenohydrocarbons, such as dichloromethane, trichloromethane, tetrachloromethane, 1,2-dichloroethane, trichloroethane, tetrachloroethane or trichloroethylene, hydrocarbons, such as benzene, xylene, toluene, hexane or cyclohexane, or petroleum fractions, nitromethane, dimethylformamide, acetonitrile or hexamethylphosphoric triamide. It is also possible to employ mixtures of the solvents. Dichloromethane is particularly preferred.

Suitable bases for the amidation are the customary basic compounds. These include, preferably, alkali metal hydroxides and alkaline earth metal hydroxides, such as lithium hydroxide, sodium hydroxide, potassium hydroxide or barium hydroxide, alkali metal hydrides, such as sodium hydride, alkali metal carbonates or alkaline earth metal carbonates, such as sodium carbonate or potassium carbonate, or alkali metal alcoholates, such as, for example, sodium methanolate or ethanolate, potassium methanolate or ethanolate or potassium tert.-butylate, or organic amines, such as benzyltrimethylammonium hydroxide, tetrabutylammonium hydroxide, pyridine, triethylamine or N-methylpiperidine.

The amidation is in general carried out in a temperature range from 0° C. to 150° C., preferably at 25° C. to 40° C.

The amidation is in general carried out under normal pressure. However, it is also possible to carry out the process under reduced pressure or under increased pressure (for example in a range from 0.5 to 5 bar).

Suitable dehydration reagents are carbodiimides, such as, for example, diisopropylcarbodiimide, dicyclohexylcarbodiimide or N-(3-dimethylaminopropyl)-N'-ethylcarbodiimide hydrochloride, or carbonyl compounds, such as carbonyldiimidazole, or 1,2-oxazolium compounds, such as 2-ethyl- 5-phenyl-1, 2-oxazolium 3-sulphonate, or propanephosphoric anhydride or isobutyl chloroformate or benzotriazolyloxy-tris-(dimethylamino)phosphonium hexafluorophosphate or phosphonic acid diphenyl ester-amide or methanesulphonyl chloride, if appropriate in the presence of bases, such as triethylamine or N-ethylmorpholine or N-methylpiperidine or dicyclohexylcarbodiimide and N-hydroxysuccinimide [compare J. C. Sheehan, S. L. LEdis, J. Am. Chem. Soc. 95, 875 (1973); F. E. Frerman et al., J. Biol. Chem. 255, 507 (1982) and N. B. Benoton, K. Kluroda, Int. Pept. Prot. Res. 13, 403 (1979), 17, 187 (1981)].

The sulphonation or sulphoamidation is carried out in the abovementioned inert solvents, if appropriate using the bases and dehydrating agents also mentioned above.

The sulphonation or sulphoamidation is in general carried out under normal pressure. However, it is also possible to carry out the processes under reduced pressure or increased pressure (for example in a range from 0.5 to 5 bar).

The sulphonation and the sulphoamidation is in general carried out in a temperature range from 0° C. to +150° C., preferably from +25° C. to +40° C.

The commercially available amines and derivatives thereof which are known from the literature are in general suitable for the amidation [compare Houben-Weyl, "Methoden der organischen Chemie (Methods of Organic Chemistry)", Volumes XI/1 and XI/2].

The sulphonation and sulphoamidation are in general likewise carried out with the customary sulphonic acids and activated derivatives thereof [compare Houben-Weyl, "Methoden der organischen Chemie (Methods of Organic Chemistry)", Volume IX, page 407 et seq.; and Beilstein 11, 26].

The esterification of the acids is carried out by the customary method, by reacting the acids with the corresponding alcohols in the presence of a catalyst, if appropriate in one of the abovementioned solvents. This alcohol is preferably also employed as the solvent.

Inorganic acids, such as, for example, sulphuric acid, or inorganic acid chlorides, such as, for example, thionyl chloride, can be employed as catalysts.

In general, 0.01 to 1, preferably 0.05 to 0.5 mol, of catalyst is employed per mole of reactant.

Both the esterification and the amidation can proceed, if appropriate, via activated stages of the carboxylic acids, such as, for example, acid halides, which can be prepared from the corresponding acid by reaction with thionyl chloride, phosphorus trichloride, phosphorus pentachloride, phosphorus tribromide or oxalyl chloride.

The acid addition salts of the compounds of the formula (I) can be obtained in a simple manner by customary salt formation methods, for example by dissolving a compound of the formula (I) in a suitable solvent and adding the acid, f or example hydrochloric acid, and they can be isolated in a known manner, for example by filtration, and if appropriate purified by washing with an inert organic solvent.

The compounds of the general formula (II) are mostly new, in particular the corresponding cis isomers, and can be prepared by a process in which compounds of the general formula (VI)

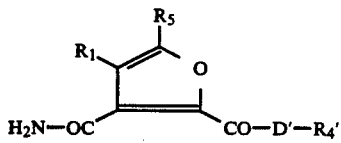

in which $R^1$, $R^{4'}$, $R^5$ and $D'$ have the abovementioned meaning, are reduced in the presence of ruthenium by a method which is known from the literature, preferably by catalytic hydrogenation (compare Polym. J. 7, 72 (1975)].

The compounds of the general formula (VI) are known per se or can be prepared by the customary methods [compare JACS, 77, 1055, 4069].

The compounds of the general formula (III) are new and can be prepared by the abovementioned process.

The compounds of the general formula (IV) are new and can be prepared by a process in which compounds of the general formula (VII)

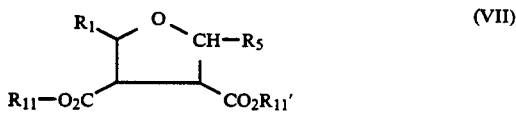

in which $R^1$ and $R^5$ have the abovementioned meaning and $R^{11}$ and $R^{11'}$ are identical or different and represent a $C_1$-$C_4$-alkyl radical, are first hydrolysed with alkali metal hydroxides, such as sodium, potassium or lithium hydroxide, preferably lithium hydroxide, in a solvent mixture, preferably tetrahydrofuran and water, to give the corresponding carboxylic acids, these are then reacted with propionic anhydride in a temperature range from $+80°$ C. to $+180°$ C., preferably at 150° C., to give the compounds of the general formula (VIII)

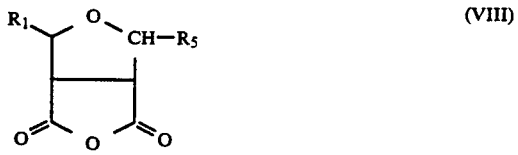

in which $R^1$ and $R^5$ have the abovementioned meaning, and in a last step, these compounds are reacted with compounds of the general formula (IX)

(R$^{10}$)$_3$SiN$_3$  (IX)

in which $R^{10}$ has the abovementioned meaning, in a temperature range from $+20°$ C. to $+80°$ C., preferably at 80° C.

The compounds of the general formula (VII) are known in some cases [compare EP 22 086; J. Chem. Soc., Perkin Trans u2 (6), 875–886; Org. Coat. Plast. Chem. 44, 108–114; J. Macromol. Sci. Chem. A 13 (4), 477–501] or are new, in which case they can be prepared by the abovementioned process.

The compounds of the general formula (VIII) are mostly new and can be prepared, f or example, by the above-mentioned process.

The compounds of the general formula (IX) are known per se or can be prepared by the customary method [compare, for example, Fieser 1, 1236; 3, 316; 5, 719; 6, 632; 7, 394; 9, 21 or 10, 14].

The compounds of the general formula (V) and (Ia) are likewise new and can be prepared by the abovementioned process.

The above preparation processes are described merely for illustration. The preparation of the compounds of the general formula (I) according to the invention is not limited to these processes, and any modification of these processes can be used in the same way for the preparation.

The compounds of the general formula (I) according to the invention and their acid addition salts have antimicrobial and, in particular, potent antimycotic actions. They have a very broad antimycotic action spectrum, in particular against dermatophytes and Blastomycetes and also biphasic fungi, for example against Candida species, such as Candida albicans, Epidermophyton species, such as Epidermophyton floccosum, Aspergillus species, such as Aspergillus niger and Aspergillus fumigatus, Trichophyton species, such as Trichophyton mentagrophytes, Microsporon species, such as Microsporon felineum, and Torulopsis species, such as Torulopsis glabrata. The enumeration of these microorganisms in no case represents a limitation of the germs which can be combated, but is only for illustrative purposes.

Examples of indications in human medicine which may be mentioned are, for example: dermatomycoses and systemic mycoses caused by *Trichophyton mentagrophytes* and other Trichophyton species, Microsporon species and also *Epidermophyton floccosum*, Blastomycetes and biphasic fungi, and also moulds.

Indication areas which may be mentioned as examples in veterinary medicine are: all dermatomycoses and systemic mycoses, in particular those which are induced by the abovementioned pathogens.

The compounds according to the invention were tested for their antimycotic in vivo activity in the intravenous, subcutaneous and oral modes of administration on the model of candidosis in mice: Male CF$_1$-SPF mice were infected with 1–3×10$^6$ germinating cells of C. albicans per animal by injection of the germ suspension in physiological NaCl solution (0.2 ml/animal) into the tail vein. Untreated control animals develop renal candidosis under these infection conditions and 95–100% of the animals employed die from this infection within 6 days post-infection. When infected animals were treated twice daily, starting with the day of infection, with the compounds according to the invention orally or parenterally in doses of 2×25 to 2×50 mg/kg of body weight for 2–5 days, 60×90% of the animals survived the infection in a good condition. The C. albicans germ counts in the kidneys of the infected and treated animals on the 4th day post-infection are on average two powers of ten lower than those of untreated, infected control animals.

The new active compound can be converted in a known manner into the customary formulations, such as tablets, coated tablets, pills, granules, aerosols, syrups, emulsions, suspensions and solutions, using inert, non-toxic, pharmaceutically suitable excipients or solvents. The therapeutically active compound should in each case be present here in a concentration of about 0.5 to 90% by weight of the total mixture, that is to say in amounts which are sufficient to achieve the stated dosage range.

The formulations are prepared, for example, by extending the active compounds with solvents and/or excipients, if appropriate using emulsifying agents and/or dispersing agents, and, for example in the case where water is used as a diluent, organic solvents can be used as auxiliary solvents if appropriate.

Administration is effected in the customary manner, preferably orally or parenterally, i particular perlingually or intravenously.

In the case of parenteral use, solutions of the active compound can be employed using suitable liquid excipient materials.

In general, it has proved advantageous, in the case of intravenous administration, to administer amounts of about 0.001 to 10 mg/kg, preferably about 0.01 to 5 mg/kg of body weight to achieve effective results, and in the case of oral administration, the dosage is about 0.01 to 25 mg/kg, preferably 0.1 to 10 mg/kg of body weight.

Nevertheless, it may at times be necessary to deviate from the amounts mentioned, and in particular to do so as a function of the body weight or of the type of administration route, of the behaviour of the individual towards the medicament, of the nature of the formulation thereof and of the time or interval at which administration takes place. Thus in some cases it may be sufficient to manage with less than the abovementioned minimum amount, while in other cases the abovementioned upper limit must be exceeded. Where larger amounts are administered, it may be advisable to divide these into several individual doses over the course of the day.

STARTING COMPOUNDS

Example I

Ethyl 2,3-cis-3-carboxamido-tetrahydrofuran-2-carboxylate

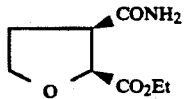

A solution of ethyl 2,3-cis-3-carboxamido-furan-2-carboxylate (1.00 g, 5.23 mmol) in 60 ml of ethanol is hydrogenated in the presence of 500 mg of rhodium-on-active-charcoal (5% strength) at 1200C under 80 bar. The mixture is filtered and washed with ethanol and the solvent is evaporated in vacuo. The residue is chromatographed on silica gel (ethyl acetate : methanol = 10:1) Yield: 0.73 g (75% of theory) $C_8H_{13}NO_4$ (187.2) Melting point: 88° C.

Example II

Ethyl 2,3-cis-3-(tert-butyloxycarbonyl)amino-tetrahydro-2-furan-carboxylate

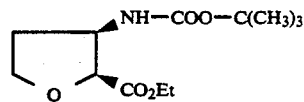

Lead(IV) acetate (1.15 g, 2.60 mmol) is added to a solution of the compound from Example I (0.45 g, 2.40 mmol) in 20 ml of tert.-butanol and the mixture is heated under reflux for 15 minutes. Triethylamine (1 ml) is added dropwise and the mixture is heated under reflux for a further 2 hours. The solvent is evaporated in vacuo, 30 ml of ether are added, the mixture is filtered and the ether is evaporated in vacuo. The residue is chromatographed on silica gel (ethyl acetate petroleum ether = 1:3). Yield: 0.208 g (33% of theory) $C_{12}H_{21}NO_5$ (259.3) Melting point: 75° C.

Example III

Tetrahydrofuran-3,4-dicarboxylic acid

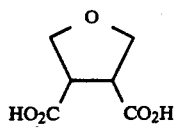

40 g (0.21 mol) of 3,4-dicarboxymethyl-tetrahydrofuran are stirred with 10.4 g (0.43 mol) of lithium hydroxide in a solvent mixture of 150 ml of tetrahydrofuran and 80 ml of $H_2O$ at room temperature for 20 hours. The tetrahydrofuran is largely distilled off and the aqueous residue is brought to pH 1 with 6 N sulphuric acid. After saturation with NaCl, the mixture is extracted with ethyl acetate, and the organic phases are combined and dried over magnesium sulphate. The filtered solution is concentrated; 23.4 g (70% of theory) of a pale oil are obtained.

$^1$H-NMR (200 MHz, DMSO): δ=3.28 (m, 2H); 3.75–4.00 (m, 4H).

Example IV (±)-cis-Tetrahydrofuran-3,4-dicarboxylic anhydride

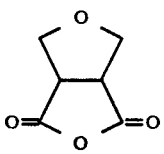

23 g (0.14 mol) of (±)-3,4-dicarboxy-tetrahydrofuran are heated at 150° C. together with 100 ml of propionic anhydride for 6.5 hours. After distillation, 11 g (54% of theory) of the target compound are obtained.

IR ($CH_2Cl_2$ solution) : 1790 and 1845 (broad) cm$^{-1}$

Example V (±)-cis-2-Isocyanato-3-carboxytrimethylsilyl-tetrahydrofuran

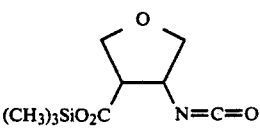

12 g (0.084 mol) of (±)-cis-tetrahydrofuran-3,4-dicarboxylic anhydride are heated slowly to 80° C. together with 13 ml (0.098 mol) of azidotrimethylsilane. After the mixture has been stirred at 80° C. for 45 minutes, it is allowed to cool and is concentrated in vacuo; 17 g (88% of theory) of the target compound, which can be further reacted without additional purification, are obtained. IR (CH$_2$Cl$_2$ solution): 1710, 1790, 2260 cm$^{-1}$.

Example VI (±)-cis-2-Amino-tetrahydrofuran-3-N-carboxylic anhydride

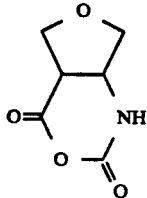

15 g (0.065 mol) of (±)-cis-2-isocyanato-3-carboxytrimethylsilyl(tetrahydrofuran) are stirred vigorously in 100 ml of diethyl ether with 0.5 ml of water for 5 minutes and the solution is then allowed to crystallize overnight at +4° C. 5.5 g (53 % of theory) of the target compound of melting point 133°-139° C. are thus obtained. MS: m/e (% relative intensity) 158 (MH+) (1); 127 (65); 55 (100).

PREPARATION EXAMPLES

Example 1

Ethyl 2,3-cis-3-amino-tetrahydro-2-furan-carboxylate hydrochloride

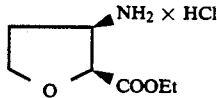

A solution of the compound from Example II (0.150 g, 0.58 mmol) in 1.5 ml of a 4 N solution of HCl in dioxane is stirred at room temperature for 2 hours. The solution is concentrated in vacuo and the residue is dried at 60° C./0.1 mm Hg for 2 hours. Yield: 0.105 g (93% of theory) C$_7$H$_{13}$NO$_3$×HCl (159.2×36.5) Melting point: 153° C.

Example 2

2,3-cis-4-Amino-tetrahydro-2-furancarboxylic acid hydrochloride

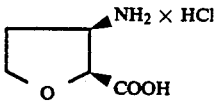

A solution of the compound from Example 1 (0.054 g / 0.28 mmol) in 5 ml of 3 N hydrochloric acid is heated under reflux for 2 hours. The solution is concentrated in vacuo and the residue is dried at 50° C./0.1 Mm Hg for 2 hours. Yield: 0.045 g (98% of theory) C$_5$H$_9$NO$_3$×HCl (131.1×36.5) Melting point: 214° C.

Example 3

(±)-cis-2-Amino-3-carboxy-tetrahydrofuran

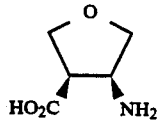

0.8 g (5 mmol) of (±)-cis-2-amino-tetrahydrofuran-3-N-carboxylic anhydride is added to 10 ml of 6 N HCl and the mixture is stirred at room temperature for 40 minutes. It is concentrated to dryness, the oily residue is taken up in 5 ml of ethanol and the mixture is stirred with 0.8 ml of propylene oxide at room temperature for 12 hours. After the product has been filtered off and dried under a high vacuum, 0.4 g (60% of theory) having a melting point of 215°-217° C. are obtained.

$^1$H-NMR (200 MHz, D$_2$O): δ=3.42 (m, -CHCO$_2$H; 1H) MS (FAB): 132 (MH+)

We claim:
1. Substituted tetrahydrofurans of the general formula (I),

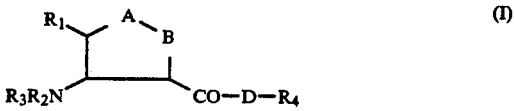

in which

A and B are always different and represent an oxygen atom, or represent the group of the formula -CHR$^5$, wherein R$^5$ denotes hydrogen or straight-chain or branched alkyl having up to 8 carbon atoms, which is optionally substituted by halogen, hydroxyl, phenyl or carboxyl or by straight-chain or branched alkoxy or alkoxycarbonyl having in each case up to 6 carbon atoms, R$^1$ represents hydrogen, or represents straight-chain or branched alkyl having up to 8 carbon atoms, which is optionally mono- or disubstituted by identical or different substituents, which may be halogen, hydroxyl, phenyl or carboxyl, or by straight-chain or branched alkoxy, acyl or alkoxycarbonyl having in each case up to 6 carbon atoms, or by a group of the formula -NR$^6$R$^7$, wherein R$^6$ and R$^7$ are identical or different and denote hydrogen, phenyl or straight-chain or branched alkyl having up to 6 carbon atoms, R$^2$ represents hydrogen, or represents straight-chain or branched alkyl having up to 8 carbon atoms, which is optionally mono- or disubstituted by identical or different substituents, which may be hydroxyl or formyl, or by straight-chain or branched acyl having up to 6 carbon atoms, or by phenyl or benzoyl, which are optionally mono- or disubstituted by identical or different substituents, which may be halogen, nitro or cyano, or by straight-chain or branched alkyl having up to 6 carbon atoms, or represents straight-chain or branched acyl having up to 8 carbon atoms, or represents benzoyl, which is optionally substituted as described above, or represents a group of the formula -SO$_2$R$^8$, wherein R⁸ denotes straight-chain or branched alkyl having up to 8 carbon atoms, benzyl or phenyl, the latter optionally being mono-, di- or trisubstituted by identical or different substituents, which may be halogen, hydroxyl, nitro, cyano, trifluoromethyl or trifluoromethoxy, or by straight-chain or branched alkyl, alkoxy or alkoxycarbonyl having in each case up to 6 carbon atoms or carboxyl, or by the abovementioned group -NR⁶R⁷, wherein R⁶ and R⁷ have the abovementioned meaning, or represents phenyl, which is optionally mono-, di- or trisubstituted by identical or different substituents, which may be halogen, hydroxyl, nitro, trifluoromethyl, trifluoromethoxy or straight-chain or branched alkyl, acyl, alkoxy or alkoxycarbonyl having in each case up to 6 carbon atoms, or by a group of the formula -NR⁶R⁷ or -SO₂R⁸, wherein R⁶, R⁷ and R⁸ have the abovementioned meaning, R³ represents hydrogen, or represents straight-chain or branched alkyl having up to 8 carbon atoms, which is optionally substituted by phenyl, or R² and R³ together represent the radical of the formula =CHR⁵', wherein R⁵' has the abovementioned meaning of R⁵ and is identical to or different from this, D represents an oxygen or sulphur atom, or represents the

group, and

R⁴ represents hydrogen, or represents straight-chain or branched alkyl having up to 8 carbon atoms or phenyl, the latter optionally being mono-, di- or trisubstituted by identical or different substituents, which may be hydroxyl, halogen, nitro, cyano, carboxyl, trifluoromethyl or trifluoromethoxy, by straight-chain or branched alkoxy, and in the case of phenyl also by alkyl, acyl or alkoxycarbonyl having in each case up to 6 carbon atoms, or by a group of the formula -NR⁶R⁷ or -SO₂R⁸, wherein R⁶, R⁷ and R⁸ have the abovementioned meaning, or, in the case where D represents the

group,

R⁴ represents the group of the formula -SO₂R⁸ wherein

R⁸ has the abovementioned meaning.

2. Substituted tetrahydrofurans of the general formula (I) according to claim 1, in which A and B are always different and represent an oxygen atom, or represent the group of the formula -CHR⁵ wherein

R⁵ denotes hydrogen or straight-chain or branched alkyl having up to 6 carbon atoms, which is optionally substituted by halogen or hydroxyl, or by straight-chain or branched alkoxy or alkoxycarbonyl having in each case up to 4 carbon atoms, R¹ represents hydrogen, or represents straight-chain or branched alkyl having up to 6 carbon atoms, which is optionally substituted by halogen or hydroxyl, by straight-chain or branched alkoxy, acyl or alkoxycarbonyl having in each case up to 4 carbon atoms, or by a group of the formula -NR⁶R⁷, wherein R⁶ and R⁷ are identical or different and denote hydrogen or straight-chain or branched alkyl having up to 4 carbon atoms, R² represents hydrogen, or represents straight-chain or branched alkyl having up to 6 carbon atoms, which is optionally substituted by hydroxyl or formyl, or by straight-chain or branched acyl having up to 4 carbon atoms, or by phenyl or benzoyl, which are optionally substituted by halogen, nitro or cyano, or by straight-chain or branched alkyl having up to 4 carbon atoms, or represents straight-chain or branched acyl having up to 6 carbon atoms, or represents benzoyl, which is optionally substituted as described above, or represents a group of the formula -SO₂R⁸, wherein R⁸ denotes straight-chain or branched alkyl having up to 6 carbon atoms, phenyl or benzyl, the latter optionally being mono- or disubstituted by identical or different substituents, which may be halogen, hydroxyl, nitro, cyano, trifluoromethyl or trifluoromethoxy, or by straight-chain or branched alkyl or alkoxy having in each case up to 4 carbon atoms, or by the abovementioned group of the formula -NR⁶R⁷, wherein R⁶ and R⁷ have the abovementioned meaning, or represents phenyl, which is optionally mono- or disubstituted by identical or different substituents, which may be halogen, hydroxyl, nitro, trifluoromethyl, trifluoromethoxy or straight-chain or branched alkyl, acyl, alkoxy or alkoxycarbonyl having in each case up to 4 carbon atoms, or by a group of the formula -NR⁶R⁷ or -SO₂R⁸, wherein R⁶, R⁷ and R⁸ have the abovementioned meaning, R³ represents hydrogen, or represents straight-chain or branched alkyl having up to 6 carbon atoms or benzyl, or R² and R³ together represent the radical of the formula =CHR⁵', wherein R⁵' has the abovementioned meaning of R⁵ and is identical to or different from this, D represents an oxygen or sulphur atom, or represents the

group, and

R⁴ represents hydrogen, or represents straight-chain or branched alkyl having up to 6 carbon atoms or phenyl, the latter optionally being mono- or disubstituted by identical or different substituents, which may be hydroxyl, halogen, nitro, cyano, trifluoromethyl or trifluoromethoxy, or by straight-chain or branched alkoxy, acyl or alkoxycarbonyl having in each case up to 4 carbon atoms, or by a group of the formula -$NR^6R^7$ or -$SO_2R^8$, wherein $R^6$, $R^7$ and $R^8$ have the abovementioned meaning, or in the case where D represents the

group, $R^4$ represents the group of the formula -$SO_2R^8$, wherein $R^8$ has the abovementioned meaning.

3. Substituted tetrahydrofurans of the general formula (I) according to claim 1, in which A and B are always different and represent an oxygen atom, or represent the group of the formula -$CHR^5$, wherein $R^5$ denotes hydrogen or straight-chain or branched alkyl having up to 4 carbon atoms, $R^1$ represents hydrogen, or represents straight-chain or branched alkyl having up to 4 carbon atoms, $R^2$ represents hydrogen, or represents straight-chain or branched alkyl having up to 4 carbon atoms, or represents straight-chain or branched acyl having up to 4 carbon atoms, or represents a group of the formula -$SO_2R^8$, wherein $R^8$ denotes straight-chain or branched alkyl having up to 4 carbon atoms, phenyl or benzyl, the latter optionally being substituted by hydroxyl, fluorine, chlorine, bromine, nitro, cyano, methyl, ethyl or methoxy, $R^3$ represents hydrogen, or represents straight-chain or branched alkyl having up to 4 carbon atoms, or $R^2$ and $R^3$ together represent the radical of the formula =$CHR^{5'}$, wherein $R^{5'}$ has the abovementioned meaning of $R^5$ and is identical to or different from this, D represents an oxygen or a sulphur atom, or represents the

group, $R^4$ represents hydrogen, or represents straight-chain or branched alkyl having up to 4 carbon atoms or phenyl, the latter optionally being substituted by fluorine, chlorine, bromine, nitro, cyano, methoxy or ethoxy, or by a group of the formula -$NR^6R^7$ or -$SO_2R^8$, wherein $R^6$ and $R^7$ are identical or different and denote hydrogen, methyl or ethyl and $R^8$ has the abovementioned meaning, or, in the case where D represents the

group, $R^4$ represents the group of the formula -$SO_2R^8$, wherein $R^8$ has the abovementioned meaning.

4. An antimycotic composition comprising an antimycotically effective amount of a compound according to claim 1 and a pharmaceutically acceptable diluent.

5. A method of combating mycoses in a patient in need thereof which comprises administering to such patient an antimycotically effective amount of a compound according to claim 1.

* * * * *